United States Patent [19]
Babler et al.

[11] Patent Number: 5,973,179
[45] Date of Patent: Oct. 26, 1999

[54] C-15 PHOSPHONATE REAGENT COMPOSITIONS FOR THE MANUFACTURE OF COMPOUNDS SUCH AS LYCOPENE AND METHODS OF SYNTHESIZING THE SAME

[75] Inventors: James H. Babler, Chicago, Ill.; Harvey W. Posvic, Carey Township, Wis.

[73] Assignee: Loyola University of Chicago, Chicago, Ill.

[21] Appl. No.: 09/195,409

[22] Filed: Nov. 19, 1998

[51] Int. Cl.[6] .............................. C07F 9/6574; C07F 9/40
[52] U.S. Cl. .............................. 558/83; 558/87; 558/122; 558/217
[58] Field of Search ....................... 558/217, 83

[56] References Cited

U.S. PATENT DOCUMENTS

| 3,197,497 | 7/1965 | Olivette | 260/461 |
|---|---|---|---|
| 5,061,819 | 10/1991 | Babler | 558/87 |
| 5,107,030 | 4/1992 | Babler | 568/494 |
| 5,471,005 | 11/1995 | Babler | 568/459 |

OTHER PUBLICATIONS

H.J. Altenbach and R. Korff, *Tetrahedron Lett.*, 1981, 22, 5175.
Babler, U. S. Patent application Serial No. 08/975819, filed Nov. 11, 1997.
Babler et al., U.S. Patent application Serial No. 09/161,983, filed on Sep. 19, 1998.
K. Bernhard and H. Mayer, *Pure & Appl. Chem.*, 1991, 63, 35.
"Carotenoids; vol. 2: Synthesis," edited by G. Britton, et al. (Birkhauser Verlag, Basel, 1996), p. 259.
*Chem. Abstracts* 1965, 63, 13318d of U.S. Patent No. 3,197,497.
*Chem. Abstracts* 1990, 112 91375w.
*Chem. Abstracts* 1991, 114, 82198e of European Patent Application EP 382,067.
*Chem. Abstracts* 1991, 115, 214528v.
H. Gerster, *J. Am. Coll. Nutr.* 1997, 16, 109.
E. Giovannucci, et al., *J. Natl. Cancer Inst.* 1995, 87, 1767.
T. Hirabe, et al., *J. Org. Chem.,* 49, 4084 (1984).
O. Isler, *Carotenoids,* Birkhauser–Verlag, pp. 431–36 (1971).
O. Isler, et al., *Helv. Chim. Acta* 1956, 39, 463.
O. Isler, et al., *Helv. Chim. Acta* 1961, 44, 985.
Johnson and Schneider, *Org. Synth.,* 30, 18 (1950).
P. Karrer, et al., *Helv. Chim. Acta* 1950, 33, 1349.
Levy, et al., *Nutr. Cancer* 1995, 24, 257.
K. Meyer, et al., *Helv. Chim. Acta* 1992, 75, 1848.
J. Michalski, et al., *J. Chem. Soc.,* 1961, 4904.
*Organic Syntheses,* Collective vol. 3, p. 747.
C.J. Palmer, et al., *Tetrahedron Lett.* 1990, 31, 2857.
B.C. Ranu, et al., *J. Org. Chem.,* 63, 5250 (1998).
B.C. Ranu et al., *Tetrahedron Lett.,* 1994, 35, 8649.
M.J. Szwedo, Jr., Studies Directed Towards the Total Synthesis of Retinoids, Ph.D. Dissertation, Loyola University of Chicago, 1983, pp. 24 & 57–58.
B.C.L. Weedon, et al., *J. Chem. Soc.* 1965, 2019.

*Primary Examiner*—Michael G. Ambrose
*Attorney, Agent, or Firm*—Marshall, O'Toole, Gerstein, Murray & Borun

[57] ABSTRACT

The present invention describes novel phosphonate reagent compositions of the formula:

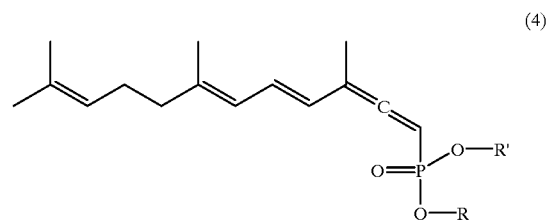

(4)

wherein R and R'=$C_1$–$C_4$ alkyl groups, or R, R'=$(CH_2)_n$ (n=2 or 3) or [$CH_2C(CH_3)_2CH_2$].

The invention also describes allylic C-15 phosphonate compounds of the formula:

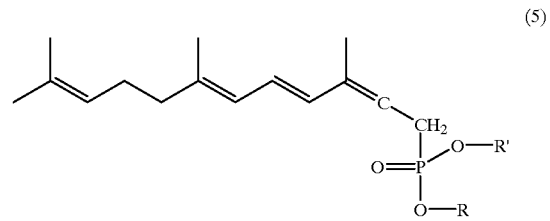

(5)

wherein R and R'=$C_1$–$C_4$ alkyl groups.

The invention also describes methods of preparing phosphonate reagent compositions (4), allylic phosphonate compounds (5), and lycopene.

27 Claims, No Drawings

C-15 PHOSPHONATE REAGENT COMPOSITIONS FOR THE MANUFACTURE OF COMPOUNDS SUCH AS LYCOPENE AND METHODS OF SYNTHESIZING THE SAME

BACKGROUND OF THE INVENTION

1. Field of the Invention

The present invention describes novel phosphonate reagent compositions of the formula:

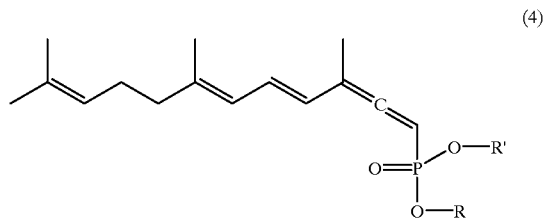

(4)

wherein R and R'=$C_1$–$C_4$ alkyl groups, or R, R'=$(CH_2)_n$ (n=2 or 3) or $[CH_2C(CH_3)_2CH_2]$.

Also described are novel methods for forming allenic C-15 phosphonate reagent compositions (4) from ethynyl-pseudoionone (3) (systematically named as 3,7,11-trimethyl-4,6,10-dodecatrien-1-yn-3-ol).

Allenic reagent compositions (4) can be partially hydrogenated to form allylic C-15 phosphonate compounds of the formula:

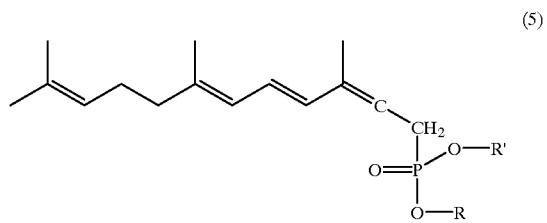

(5)

wherein R and R'=$C_1$–$C_4$ alkyl groups.

Phosphonate compounds (5) can be employed as precursors to a variety of biologically-active materials, including lycopene (7). Accordingly, the invention also describes a four-step route for the conversion of pseudoionone (2) to lycopene (7).

2. Description of Related Art (a) Prior Art Processes for Preparation of Lycopene and Utility of Lycopene There are approximately 600 naturally occurring carotenoids, but only six of these have so far been produced industrially. Insofar as applicants are aware, the only companies that manufacture synthetic "nature-identical" carotenoids at the present time are Roche (since 1954) and BASF (since 1960). Sales of such compounds are growing rapidly and in 1995 surpassed 500 million U.S. dollars. [Reference: "Carotenoids; Volume 2: Synthesis," edited by G. Britton, et al. (Birkhauser Verlag, Basel, 1996), page 259]. This reference indicates that the symmetrical acyclic $C_{40}$-carotenoid lycopene (7), which is the red coloring matter of tomatoes, has potential commercial value. Indeed, chemists at Roche have recently developed an industrially feasible synthesis of lycopene, although it requires the use of a very costly raw material (triphenylphosphine). See: K. Meyer, et al., *Helv. Chim. Acta* 1992, 75, 1848.

Compared to β-carotene, lycopene exhibits higher radical scavenging properties, which makes it an interesting candidate for antioxidant activity studies in humans [H. Gerster, *J. Am. Coll. Nutr.* 1997, 16, 109]. Levy and coworkers [*Nutr. Cancer* 1995, 24, 257] showed the inhibitory effect of lycopene on the growth of human endometrial, mammary, and lung cancer cells; and it has been verified that a lycopene-rich diet decreases the risk of prostate cancer [E. Giovannucci, et al., *J. Natl. Cancer Inst.* 1995, 87, 1767]. Indeed, it is now thought that lycopene is important in giving protection against a variety of serious disorders including cancer, heart disease, and degenerative eye diseases. For example, lycopene is known to be an antitumor agent against brain tumors [*Chem. Abstracts* 1990, 112 91375w]. Also interesting is the report in a recent Japanese patent [*Chem. Abstracts* 1991, 115, 214528v] that a topical solution of lycopene controls acne and also markedly promotes hair growth in mice.

The first synthesis of lycopene (7) was reported in 1950 [P. Karrer, et al., *Helv. Chim. Acta* 1950, 33, 1349], but suffered from a low overall yield (0.1%) starting with pseudoionone (2). Subsequent syntheses of lycopene starting with pseudoionone proceeded in overall yields as high as 20% [e.g., B. C. L. Weedon, et al., *J. Chem. Soc.* 1965, 2019]. However, all such syntheses required too many steps and/or the use of costly raw materials (e.g., triphenylphosphine). Other syntheses of lycopene can be found in: O. Isler, et al., *Helv. Chim. Acta* 1956, 39, 463; K. Bernhard and H. Mayer, *Pure & Appl. Chem.* 1991, 63, 35; and *Chem. Abstracts* 1991, 114, 82198e.

(b) Prior Art Processes for Forming Pseudoionone

A preliminary step in a preferred method for preparing the compounds of the present invention involves the preparation of pseudoionone (2) [IUPAC name: 6,10-dimethyl-undeca-3,5,9-trien-2-one]. This specialty chemical can be prepared by a crossed-aldol condensation of citral (1) [IUPAC name: 3,7-dimethylocta-2,6-dienal] with acetone:

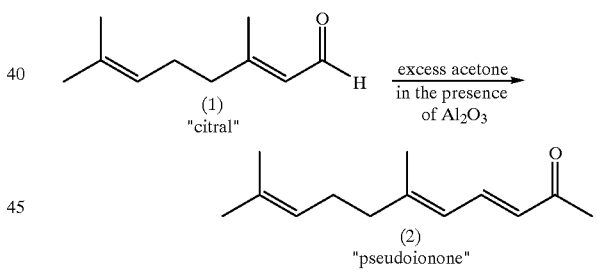

Alternatively, pseudoionone (2) can be prepared by the following four-step route starting with isoprene (as disclosed in Babler et al., U.S. patent application Ser. No. 09/161,983, filed on Sep. 19, 1998, the disclosure of which is hereby incorporated by reference):

(A)

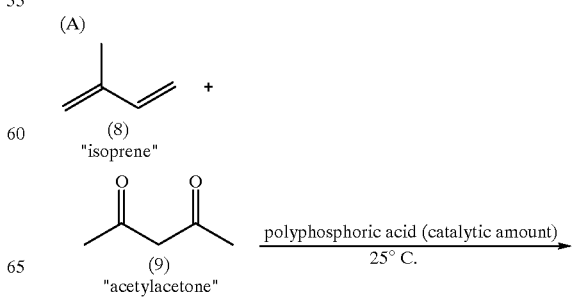

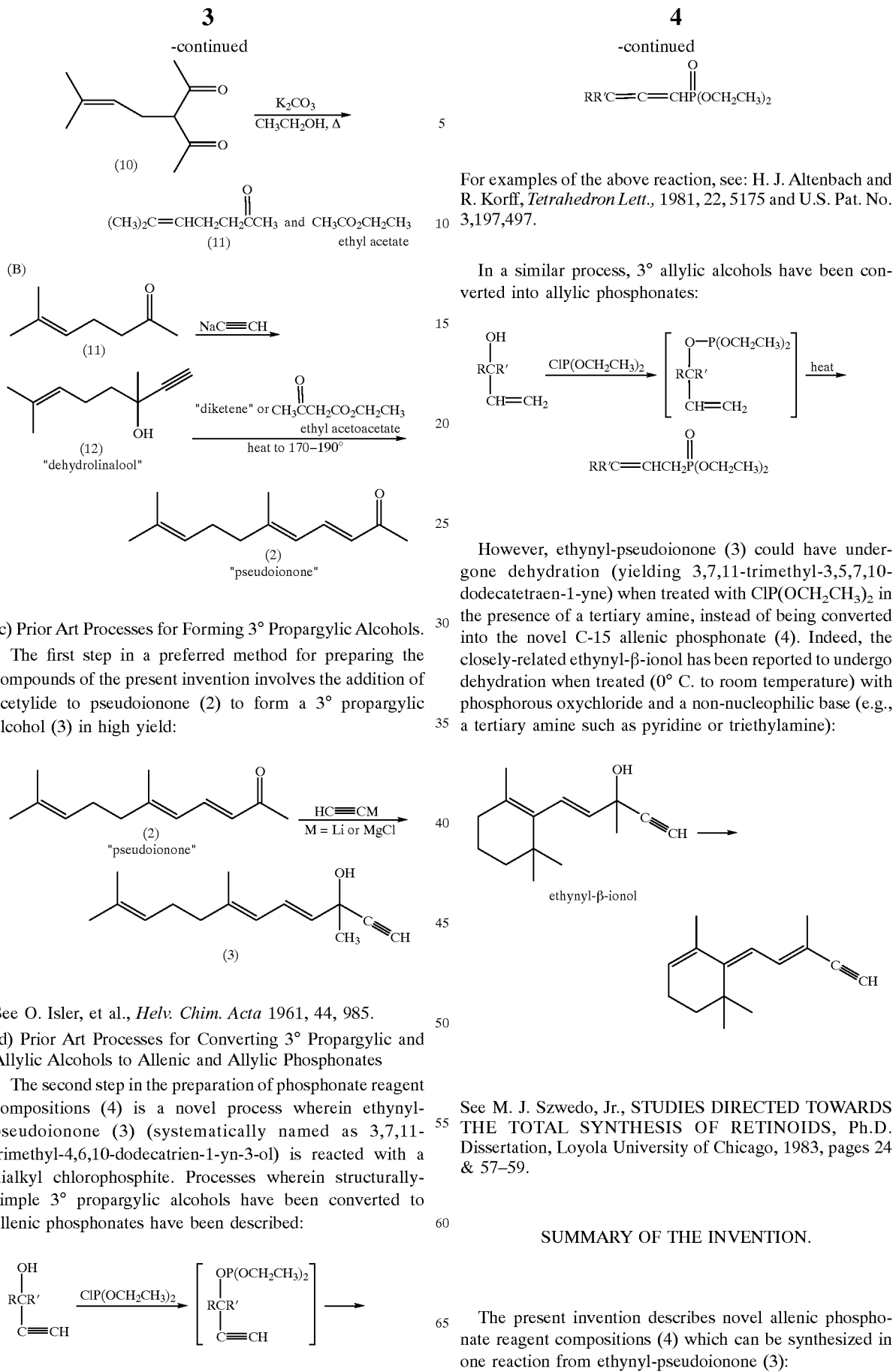

For examples of the above reaction, see: H. J. Altenbach and R. Korff, *Tetrahedron Lett.,* 1981, 22, 5175 and U.S. Pat. No. 3,197,497.

In a similar process, 3° allylic alcohols have been converted into allylic phosphonates:

However, ethynyl-pseudoionone (3) could have undergone dehydration (yielding 3,7,11-trimethyl-3,5,7,10-dodecatetraen-1-yne) when treated with $ClP(OCH_2CH_3)_2$ in the presence of a tertiary amine, instead of being converted into the novel C-15 allenic phosphonate (4). Indeed, the closely-related ethynyl-β-ionol has been reported to undergo dehydration when treated (0° C. to room temperature) with phosphorous oxychloride and a non-nucleophilic base (e.g., a tertiary amine such as pyridine or triethylamine):

(c) Prior Art Processes for Forming 3° Propargylic Alcohols.

The first step in a preferred method for preparing the compounds of the present invention involves the addition of acetylide to pseudoionone (2) to form a 3° propargylic alcohol (3) in high yield:

See O. Isler, et al., *Helv. Chim. Acta* 1961, 44, 985.

(d) Prior Art Processes for Converting 3° Propargylic and Allylic Alcohols to Allenic and Allylic Phosphonates The second step in the preparation of phosphonate reagent compositions (4) is a novel process wherein ethynyl-pseudoionone (3) (systematically named as 3,7,11-trimethyl-4,6,10-dodecatrien-1-yn-3-ol) is reacted with a dialkyl chlorophosphite. Processes wherein structurally-simple 3° propargylic alcohols have been converted to allenic phosphonates have been described:

See M. J. Szwedo, Jr., STUDIES DIRECTED TOWARDS THE TOTAL SYNTHESIS OF RETINOIDS, Ph.D. Dissertation, Loyola University of Chicago, 1983, pages 24 & 57–59.

SUMMARY OF THE INVENTION.

The present invention describes novel allenic phosphonate reagent compositions (4) which can be synthesized in one reaction from ethynyl-pseudoionone (3):

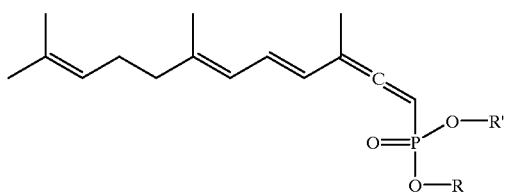

(4)

wherein R and R'=C₁–C₄ alkyl groups, or

R, R'=(CH₂)ₙ (n=2 or 3) or [CH₂C(CH₃)₂CH₂].

When R and R' are alkyl groups having up to four carbon atoms, the compounds of the invention are systematically named as esters of an alkapentaenylphosphonic acid. For example, when R=R'=ethyl, the compound is named:

3,7,11-trimethyl-1,2,4,6,10-dodecapentaenylphosphonic acid, diethyl ester.

Other compounds within the scope of the present invention include:

3,7,11-trimethyl-1,2,4,6,10-dodecapentaenylphosphonic acid, dimethyl ester;

3,7,11-trimethyl-1,2,4,6,10-dodecapentaenylphosphonic acid, diisopropyl ester;

3,7,11-trimethyl-1,2,4,6,10-dodecapentaenylphosphonic acid, dipropyl ester; and 3,7,11-trimethyl-1,2,4,6,10-dodecapentaenylphosphonic acid, dibutyl ester.

Phosphonate reagents (4) also include C-15 allenic phosphonate compounds in which R and R' form part of a 5- or 6-membered heterocyclic ring. Thus, for example, when R, R'=CH₂CH₂, the compound is named 2-(3,7,11-trimethyldodeca-1,2,4,6,10-pentaenyl)-1,3,2-dioxaphospholan-2-one:

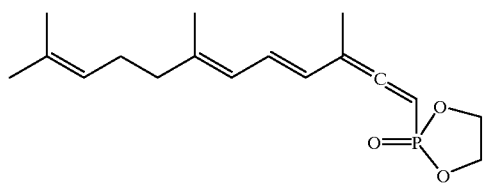

The present invention also describes novel C-15 allylic phosphonates (5), which can be represented by the following formula:

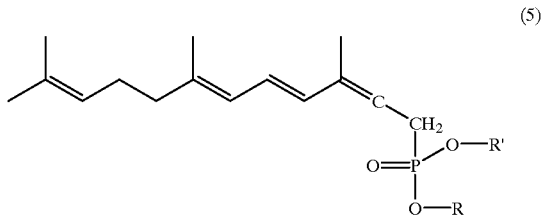

(5)

wherein R and R'=C₁–C₄ alkyl groups.

As described in more detail below, allylic phosphonates (5) can be prepared by partial reduction of the phosphonate reagents (4). The allylic phosphonates (5) are named as ester derivatives of an alkatetraenylphosphonic acid. Thus, for example when R=R'=ethyl, the compound is named:

3,7,11-trimethyl-2,4,6,10-dodecatetraenylphosphonic acid, diethyl ester.

Other compounds within the scope of the present invention include:

3,7,11-trimethyl-2,4,6,10-dodecatetraenylphosphonic acid, dimethyl ester;

3,7,11-trimethyl-2,4,6,10-dodecatetraenylphosphonic acid, diisopropyl ester;

3,7,11-trimethyl-2,4,6,10-dodecatetraenylphosphonic acid, dipropyl ester;

3,7,11-trimethyl-2,4,6,10-dodecatetraenylphosphonic acid, dibutyl ester; and 3,7,11-trimethyl-2,4,6,10-dodecatetraenylphosphonic acid, ethyl beta-hydroxyethyl diester.

The invention also describes methods for preparing allenic phosphonate reagent compositions (4) and allylic phosphonates (5). The invention also relates to a four-step route for the conversion of pseudoionone (2) to lycopene (7). Attractive features of this route to lycopene include: the route does not require any oxidative transformations; it avoids the use of organic halides and metals (other than sodium); all steps proceed in high yield; and all raw materials necessary for this route are low-cost compounds which are manufactured on an industrial scale.

A method of preparing allenic phosphonate reagent compositions (4) includes the following steps:

(I) forming a reaction mixture in an aprotic solvent comprising:
  (a) ethynyl-pseudoionone;
  (b) at least one molar equivalent of a non-nucleophilic base; and
  (c) at least one molar equivalent of a dialkyl chlorophosphite reagent; and (II) maintaining the reaction mixture until the allenic phosphonate is formed.

A method of preparing allylic phosphonates (5) includes the following steps:

(I) forming a first reaction mixture in an aprotic solvent comprising:
  (a) ethynyl-pseudoionone;
  (b) at least one molar equivalent of a non-nucleophilic base; and
  (c) at least one molar equivalent of a dialkyl chlorophosphite reagent;

(II) maintaining the first reaction mixture until the allenic phosphonate is formed; and (III) partially reducing the allenic phosphonate of step II.

The partial reduction step (III) may include the steps of forming a second reaction mixture in an alcohol solvent including the allenic phosphonate of step II, ammonium formate, and 10% Pd—C; and vigorously agitating the second reaction mixture while heating it to a temperature in excess of room temperature. The partial reduction step (III) may include the step of forming a second reaction mixture including the allenic phosphonate of step II and sodium borohydride.

The methods for preparing compounds (4) and (5) are analogous to reactions disclosed in Babler, U.S. patent application Ser. No. 08/975,819 filed Nov. 21, 1997, the disclosure of which is hereby incorporated by reference.

The methods for preparing an allenic phosphonate reagent composition (4), an allylic phosphonate (5), and lycopene (7) are summarized by the following reaction sequence:

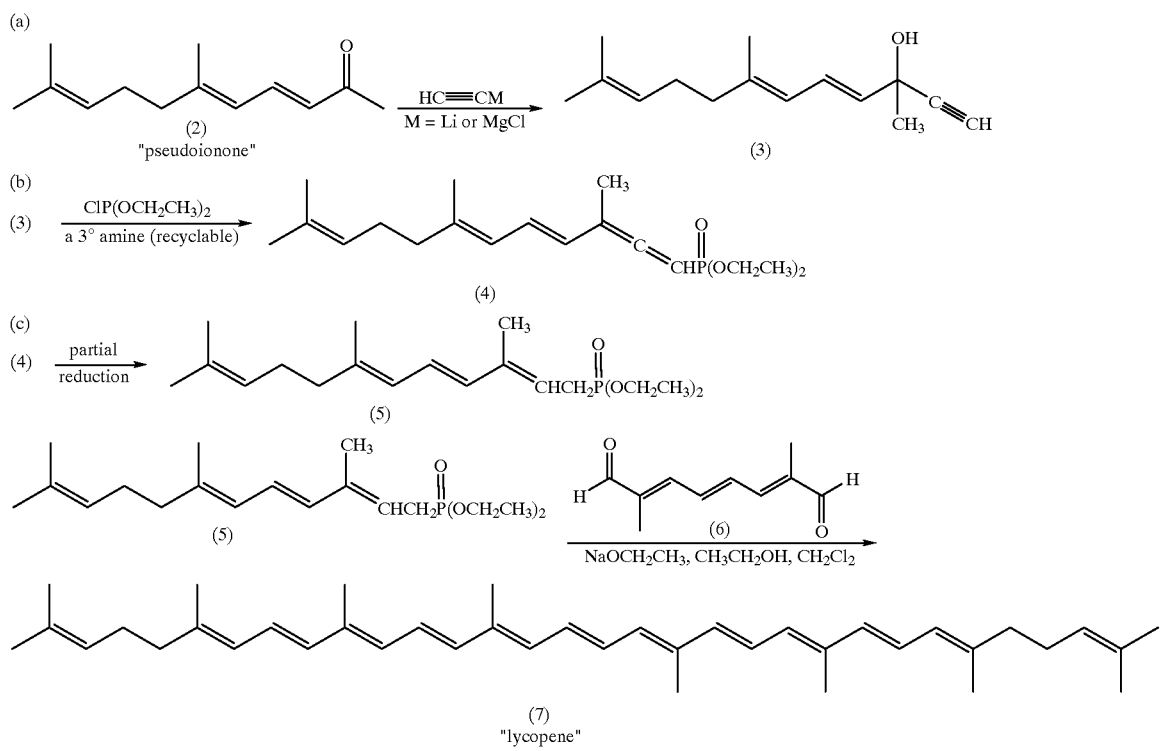

Step (b) of the reaction sequence—the conversion of ethynyl-pseudoionone (3) to phosphonate reagent compositions (4)—utilizes a reagent with a phosphorus-chlorine bond in the presence of a 3° amine. This conversion requires:

(A) ethynyl-pseudoionone (3) in an aprotic organic solvent;

(B) the presence of at least one molar equivalent of a non-nucleophilic base: tertiary amines such as pyridine or triethylamine, $Na_2CO_3$ and $K_2CO_3$ are especially preferred; and (C) addition of one molar equivalent of a dialkyl chlorophosphite reagent, $(RO)_2PCl$, to a mixture of (A) and (B): preferred phosphite reagents include diethyl chlorophosphite and 2-chloro-1,3,2-dioxaphospholane. Step (b) proceeds at reaction temperatures from approximately 0° C. to room temperature, although higher temperatures can be employed. In a preferred method, a dialkyl chlorophosphite reagent is added, dropwise, with external cooling, to a stirred reaction mixture which is maintained at approximately 0° C. under an atmosphere of a non-reactive gas (e.g., nitrogen gas). Once addition of the dialkyl chlorophosphite reagent is complete, the reaction mixture is allowed to warm up to room temperature to enable the reaction to go to completion, and the reaction proceeds rapidly (less than one hour). Upon completion, the addition of a small amount of water to the reaction mixture will destroy any unreacted dialkyl chlorophosphite reagent.

The dialkyl chlorophosphite reagent utilized in step (b) can be prepared by treating $PCl_3$ with 2 equivalents of alcohol (e.g., ethyl alcohol) in a nonpolar solvent as described by J. Michalski, et. al. in *J. Chem. Soc.,* 1961, 4904. Alternatively, the desired transformation can be effected by adding $PCl_3$ to the mixture of (A) and (B), followed by the addition of two equivalents of alcohol.

Allenic phosphonate compounds (4) can be partially reduced to form allylic phosphonate compounds (5), as depicted in step (c), above. This transformation was achieved using one equivalent of ammonium formate in methyl alcohol (chemistry analogous to that described in U.S. patent application Ser. No. 08/975,819). More conveniently, as a small-scale laboratory transformation, partial reduction of (4) to obtain (5) was achieved in quantitative yield by use of $NaBH_4$ in ethyl alcohol at room temperature—a reaction for which there is no literature precedent (i.e., $NaBH_4$ has never been utilized to reduce allenic phosphonates).

The novel route to lycopene is concluded by a modified Wittig reaction involving the alkoxide-base promoted coupling of C-15 phosphonate reagent (5) to C-10 dialdehyde (6) [IUPAC name: 2,7-dimethylocta-2,4,6-triene-1,8-dial]. Many syntheses of the latter compound (6) are known, including two routes in recent U.S. Pat. No. [5,107,030 (Apr. 21, 1992) and U.S. Pat. No. 5,471,005 (Nov. 28, 1995)] granted to J. Babler. For previous syntheses of dialdehyde (6), see: O. Isler, *Carotenoids*, Birkhauser-Verlag, pp. 431–36 (1971).

The selective hydrogenation of only one of the five double bonds in C-15 allenic phosphonate (4) to obtain C-15 allylic phosphonate (5), the direct precursor to lycopene, could not be predicted in advance. Initial attempts to convert (4) to (5) using 6 equivalents of ammonium formate and a palladium catalyst in methyl alcohol [as reported by B. C. Ranu, et al, *J. Org. Chem.,* 63, 5250 (1998)] resulted in reduction of the double bonds between C-4 and C-5, as well as C-1 and C-2. Indeed, the relatively unhindered disubstituted double bond between C-4 and C-5 might be easier to hydrogenate than the olefinic linkage between C-1 and C-2 (due to the presence of the bulky phosphonate group). Consistent with this concern is a report by C. J. Palmer, et al., *Tetrahedron Lett.* 1990, 31, 2857, that unhindered olefin moieties can be selectively hydrogenated in the presence of the easily reduced terminal alkyne functionality if a bulky substituent is bonded to the latter.

The other methodology used to selectively reduce one of the five double bonds in C-15 allenic phosphonate (4) to obtain C-15 allylic phosphonate (5) utilizes a metal hydride reducing agent (NaBH$_4$). No prior art directly related to that transformation ((4)→(5)) could be found. Indeed, allylic phosphonates themselves are known to be subject to reduction by use of a suitable metal hydride at room temperature. For example, see the conversion of allylic phosphonate 1 g to alkene 2 g reported by T. Hirabe, et al., *J. Org. Chem.,* 49, 4084 (1984).

DETAILED DESCRIPTION OF THE INVENTION

The following examples are presented for purposes of illustration and should not be construed as limiting the invention which is delineated in the claims.

EXAMPLE I

Preparation of 6,10-Dimethyl-3,5,9-undecatrien-2-one (pseudoionone)

1.00 mL (5.84 mmoles) of citral (purchased from Aldrich Chemical Co., Milwaukee, Wis.), 20 mL of acetone (HPLC-grade, purchased from Aldrich Chemical Co.), and 1.66 g of alumina (weakly acidic, activated, Brockmann I, 150 mesh, Aldrich catalog #26,774-0) were added to a 200 mL glass pressure bottle containing a Teflon-coated spin bar. After sweeping the bottle briefly with a stream of nitrogen gas, the bottle was closed; and the mixture was subsequently heated at 65–70° C. (external oil bath temperature) for 20 hours. After cooling the mixture to room temperature, the product was isolated by dilution of the reaction mixture with 160 mL of 3:1 (v/v) ether: dichloromethane and removal of the alumina by filtration through a small pad of Hyflo Super-Cel® filtering aid. For large-scale reactions, fractional distillation of this filtrate would be the only requirement to complete the process of isolating the product. For convenience in a small-scale reaction, the filtrate was washed three times with 140 mL portions of 5% (w/v) aqueous sodium chloride to remove 4-hydroxy-4-methyl-2-pentanone (formed in minor amounts by the self-aldol condensation of acetone), then dried over anhydrous magnesium sulfate, and filtered. Removal of the ether and dichloromethane by evaporation at reduced pressure and subsequent evaporative ("Kugelrohr oven") distillation afforded 1.03 g (91% yield) of the named unsaturated ketone: boiling point 102–110° C. (bath temperature, 0.40 mm). The identity and purity of this compound was ascertained by IR and proton NMR analysis (recorded at 400 MHz). The latter spectrum exhibited a multiplet at δ 7.42 (C-4 vinyl H), a doublet (J=14.8 Hz) at δ 6.08 (C-3 vinyl H), a doublet (J=12 Hz) at δ 6.004 (C-5 vinyl H), a multiplet at δ 5.09 (C-9 vinyl H), a singlet at δ 2.27 (CH$_3$C=O), and signals for three vinyl methyl groups at δ 1.90 (CH$_3$bonded to C-6), 1.676, and 1.606.

For an alternative procedure to convert citral to pseudoionone, see: *ORGANIC SYNTHESES*, Collective Volume 3, page 747.

EXAMPLE II

Preparation of 3,7,11-Trimethyl-4,6,10-dodecatrien-1-yn-3-ol by Treatment of Pseudoionone with Ethynylmagnesium Chloride 20 mL of 0.5 M solution of ethynylmagnesium chloride (10 mmoles) in tetrahydrofuran (purchased from Aldrich Chemical Co., Milwaukee, Wis.) was added to a 100 mL 3-neck reaction flask fitted with an addition funnel and an adapter connected to an apparatus similar to that described by Johnson and Schneider [*Org. Synth.,* 30, 18 (1950)] so that the mixture in the flask could be protected from atmospheric moisture, et al. throughout the course of the reaction. After sweeping the system briefly with a stream of nitrogen gas and placing the flask in an ice-water bath (0° C.), a solution of 926 mg (4.815 mmoles) of pseudoionone (prepared as described in Example I) in 2.50 mL of anhydrous tetrahydrofuran was added dropwise over 5 minutes to the stirred Grignard reagent. The resulting mixture was stirred at 0° C. for an additional 90 minutes; after which it was diluted with 5 mL of hexane and the excess organometallic reagent was destroyed by slow, dropwise addition of 8 mL of saturated aqueous ammonium chloride. After allowing the mixture to warm to room temperature, it was diluted with 50 mL of 1:1 (v/v) hexane: ether and 200 mL of saturated brine mixed with 5 mL of 2 M aqueous HCl. After separation from the aqueous layer, the organic layer was washed with saturated brine (2×150 mL), dried over anhydrous magnesium sulfate, and subsequently filtered. Removal of the volatile organic solvents by evaporation at reduced pressure and subsequent evaporative ("Kugelrohr oven") distillation in the presence of 10 mg of powdered CaCO$_3$ afforded 970 mg (92% yield) of the named unsaturated alcohol: boiling point 105–120° C. (bath temperature, 0.25 mm). The identity and purity of this compound was ascertained by IR and proton NMR analysis (recorded in CDCl$_3$ solution at 300 MHz). The latter spectrum exhibited a multiplet at δ 6.748 (C-4 vinyl H), a doublet (J=10.8 Hz) at δ 5.840 (C-6 vinyl H), a doublet of doublets (J=15, 10.8 Hz) at δ 5.662 (C-5 vinyl H), a multiplet at δ 5.096 (C-10 vinyl H), a singlet at δ 2.582 (C≡CH), and a singlet at δ 1.579 (CH$_3$ bonded to C-3). An alternate route to this same alkynol can be found in R. Ruegg, et al., *Helv-. Chim. Acta,* 44, 985 (1961).

EXAMPLE III

Preparation of 3,7,11-Trimethyl-1,2,4,6,10-dodecapentaenylphosphonic acid, Diethyl Ester To a 15 mL 2-neck reaction flask fitted with an adapter connected to an apparatus similar to that described by Johnson and Schneider [*Org. Synth.,* 30, 18 (1950)] so that the mixture in the flask could be protected from atmospheric moisture, et al. throughout the course of the reaction were added 328 mg (1.502 mmoles) of distilled alkynol prepared as described in Example II, 0.50 mL (3.59 mmoles) of triethylamine (purchased from Aldrich Chemical Co., Milwaukee, Wis.), 2 mg of hydroquinone (or other suitable antioxidant), and 3.5 mL of dichloromethane (A.C.S. reagent-grade, purchased from Aldrich Chemical Co.). After placing the flask in an ice-water bath (0° C.), 0.35 mL (2.42 mmoles) of diethyl chlorophosphite (95%, purchased from Aldrich Chemical Co.) was added dropwise via syringe while simultaneously maintaining the stirred reaction mixture under a gentle stream of nitrogen gas. The resulting mixture was stirred at 0° C. for an additional 10 minutes and subsequently at room temperature for 75 minutes. The mixture was then cooled to approximately 0° C. by means of an external ice-water bath, and 0.10 mL of water was added to destroy any unreacted diethyl chlorophosphite. After dilution of the mixture with 45 mL of 2:1 (v/v) hexane:dichloromethane, the organic layer was washed in successive order with 25 mL portions of 10% aqueous sodium chloride and saturated brine. The organic extracts were then dried over anhydrous magnesium sulfate and subsequently filtered. Removal of the volatile organic solvents by evaporation at reduced pressure, subsequent addition of 5 mL of benzene to the residual material, and removal of the benzene accompanied by trace amounts of triethylamine under reduced pressure afforded 511 mg of crude product. The latter material was purified via chromatography on Florisil (20 mL, 60–100 mesh). After removal of any non-polar impurities by washing the column with 60 mL of 19:1 (v/v) hexane:ether, the named phosphonate (428 mg, 84% yield) was eluted using 100 mL of 1:1(v/v) ether:dichloromethane. The identity and purity of this compound were ascertained by IR (1935 cm$^{-1}$, C=C=C) and proton NMR analysis (recorded in CDCl$_3$ solution at 300 MHz). The latter spectrum exhibited a singlet (broad) at δ 5.48 (C-1 vinyl H), a multiplet at δ 5.092 (C-10 vinyl H), a multiplet at δ 4.098 (two OCH$_2$ moieties), a broad singlet at δ 1.92 (CH$_3$ bonded to C-3), singlets at δ 1.797, 1.681 and 1.607 (the other three vinyl CH$_3$'s), and a triplet (J=7.2 Hz) at δ 1.321 (2×CH$_3$ in the phosphonate moiety). In order to prevent aerobic oxidation of this unsaturated phosphonate, it should be stored in the presence of a small amount of a suitable antioxidant (e.g., hydroquinone).

NOTE: In lieu of purchasing diethyl chlorophosphite from Aldrich Chemical Co., it can be prepared from phosphorus trichloride and ethyl alcohol in accordance with a procedure suggested by J. Michalski, et al., *J. Chem. Soc.*, 4904 (1961).

EXAMPLE IV

Partial Reduction of 3,7,11-Trimethyl-1,2,4,6,10-dodecapentaenylphosphonic Acid, Diethyl Ester In accordance with a procedure suggested by B. C. Ranu, et al., *J. Org. Chem.*, 63, 5250 (1998), the following experiment was conducted: To a 25-mL 1-neck reaction flask fitted with a reflux condenser connected to an apparatus similar to that described by Johnson and Schneider [*Org. Synth.*, 30, 18 (1950)] so that the mixture in the flask could be protected from atmospheric moisture, et al. throughout the course of the reaction were added 135 mg (0.40 mmole) of allenic phosphonate produced in accordance with Example III, 1 mg of hydroquinone (or other suitable antioxidant), 4.0 mL of methyl alcohol (HPLC-grade, purchased from Aldrich Chemical Co.), 148 mg (2.35 mmoles) of ammonium formate (purchased from Aldrich Chemical Co.), and 21 mg of 10% Pd—C (available from Aldrich Chemical Co.). After sweeping the system briefly with nitrogen gas, the mixture was heated, with vigorous stirring, at 60–65° C. (external oil bath temperature) for 20 hours. After cooling the mixture to room temperature, the product was isolated by dilution of the reaction mixture with 25 mL of 4:1 (v/v) ether:dichloromethane and removal of the palladium catalyst by filtration through a small pad of Hyflo Super-Cel® filtering aid. The filtrate was subsequently washed with saturated brine (2×50 mL), then dried over anhydrous magnesium sulfate and filtered. Removal of the ether and dichloromethane by evaporation at reduced pressure afforded 120 mg (88% yield, not corrected for over-reduction) of a mixture of unsaturated phosphonates. IR analysis of the latter indicated that the double bond between C-1 and C-2 had been reduced [i.e., lack of absorption at 1935 cm$^{-1}$ arising from the allenic moiety (C=C=C)]; however, proton NMR analysis indicated that some over-reduction (i.e., hydrogenation of the double bond between C-4 and C-5) had occurred. Although over-reduction could be prevented by use of a stoichiometric amount (i.e., 1–1.2 equivalents) of ammonium formate under similar reaction conditions, the process was quite slow. For small-scale experiments, it was more convenient to effect the partial reduction of the named allenic phosphonate by use of sodium borohydride in ethyl alcohol as described in Example V.

EXAMPLE V

Preparation of 3,7,11-Trimethyl-2,4,6,10-dodecatetraenylphosphonic Acid, Diethyl Ester To a 25 mL reaction flask fitted with an adapter connected to an apparatus similar to that described by Johnson and Schneider [*Org. Synth.*, 30, 18 (1950)] so that the mixture in the flask could be protected from atmospheric moisture, et al. throughout the course of the reaction were added 272 mg (0.80 mmole) of allenic phosphonate produced in accordance with Example III, 4.0 mL of absolute ethanol, and 60 mg (1.59 mmoles) of sodium borohydride (purchased from Aldrich Chemical Co., Milwaukee, Wis.). This mixture was subsequently stirred at room temperature for 3 hours. The product was isolated after dilution of the reaction mixture with 30 mL of 2:1 (v/v) hexane:dichloromethane and subsequent washing of the organic layer in successive order with 5% (w/v) aqueous sodium chloride (50 mL) and 10% (w/v) aqueous sodium chloride (2×40 mL). The organic layer was then dried over anhydrous magnesium sulfate and subsequently filtered. Removal of the volatile organic solvents by evaporation at reduced pressure afforded 265 mg (97% yield) of the named allylic phosphonate. The identity of this compound was confirmed by proton NMR analysis (recorded in CDCl$_3$ solution at 400 MHz). The latter spectrum exhibited a doublet of doublets (J=22.5, 8.4 Hz) at δ 2.72 (CH$_2$P). IR analysis of the product confirmed the absence of any unreacted starting compound (i.e., no absorption at 1935 cm$^{-1}$).

EXAMPLE VI

Preparation of 2-(3,7,11-Trimethyldodeca-1,2,46,10-pentaenyl)-1,3,2-dioxaphospholan-2-one The reaction was conducted in the manner described in the procedure of Example III using the following reagents: 292 mg (1.34 mmoles) of distilled 3,7,11-trimethyl-4,6,10-dodecatrien-1-yn-3-ol (produced in accordance with Example II), 1.5 mg of hydroquinone, 0.35 mL (2.51 mmoles) of triethylamine, 2.50 mL of dichloromethane (A.C.S. reagent-grade), and 150 microliters (1.69 mmoles) of 2-chloro-1,3,2-dioxaphospholane (purchased from Aldrich Chemical Co., Milwaukee, Wis.). Isolation of the product as described in the procedure of Example III afforded (with no need for purification by chromatography) 372 mg (90% yield) of the named allenic phosphonate. The identity and purity of this compound were ascertained by IR (1935 cm$^{-1}$, C=C=C) and proton NMR analysis (recorded in CDCl$_3$ solution at 300 MHz). The latter spectrum exhibited a broad singlet at δ 5.587 (C-1 vinyl H), a multiplet at δ 5.083 (C-10 vinyl H), two multiplets at δ 4.43 and 4.20 (OCH$_2$CH$_2$O), a multiplet at δ 1.930 (CH$_3$ bonded to C-3), a singlet at δ 1.797 (CH$_3$ bonded to C-7), and two broad singlets at δ 1.678 and 1.602 (the other two vinyl CH$_3$'s). Storage of this compound in the presence of a small amount of a suitable antioxidant (e.g., hydroquinone) is recommended.

EXAMPLE VII

Partial Reduction of 2-(3,7,11-Trimethyldodeca-1,2, 4,6,10-pentaenyl)-1,3,2-dioxaphospholan-2-one The reaction was conducted in the manner described in the procedure of Example V using the following reagents: 196 mg (0.636 mmole) of the above-named allenic phosphonate (produced in accordance with Example VI), 4.0 mL of absolute ethyl alcohol, and 47 mg (1.24 mmoles) of sodium borohydride. Isolation of the product as described in the procedure of Example V afforded 207 mg of a phosphonate that was shown by IR and proton NMR analysis (300 MHz) to have a structure different from the anticipated 2-[3,7,11-trimethyldodeca-2,4,6,10-tetraenyl]-1,3,2-dioxaphospholan-2-one. The product was identified as 3,7,11-trimethyl-2,4,6,10-dodecatetraenyl-phosphonic acid, ethyl beta-hydroxyethyl diester—an allylic phosphonate that can still be used in the synthesis of lycopene. The formation of this product can be explained by the facile ethanolysis of the strained heterocyclic ring (i.e., a 1,3,2-dioxaphospholan-2-one) present in the starting material. The proton NMR spectrum of this product exhibited a multiplet at δ 4.124 (4H's, 2×POCH$_2$), a multiplet at δ 3.777 (CH$_2$bonded to an OH), a doublet of doublets (J=23.1, 8.4 Hz) at δ 2.78 (CH$_2$P), and a triplet (J=6.9 Hz) at δ 1.31 (CH$_3$ in the phosphonate moiety).

EXAMPLE VIII

Preparation of Lycopene

To a solution of 211 mg (0.62 mmole) of 3,7,11-trimethyl-2,4,6,10-dodecatetraenylphosphonic acid, diethyl ester (produced in accordance with Example V) and 40 mg (0.24 mmole) of 2,7-dimethyl-2,4,6-octatrienedial (prepared as described in Example XIV of U.S. Pat. No. 5,061,819) in 2.25 mL of 8:1 (v/v) anhydrous tetrahydrofuran:dimethyl sulfoxide, protected from atmospheric moisture and maintained at a temperature of approximately 50° C. by use of an external ice water bath was added 70 mg (0.62 mmole) of potassium tert-butoxide. This mixture was subsequently stirred in the cold for 15 minutes and then at room temperature for 3 hours. The product was isolated by dilution of the mixture with 25 mL of chloroform and subsequent washing of the organic layer with 5% (w/v) aqueous sodium chloride (3×25 mL). The organic layer was then dried over anhydrous magnesium sulfate and filtered. Removal of the volatile organic solvents by evaporation at reduced pressure, followed by filtration through a small column of Florisil (10 mL, 60–100 mesh, elution with 90 mL of benzene) to remove any unreacted starting materials afforded 70 mg (54% yield) of lycopene, the identity of which was confirmed by proton NMR analysis (recorded in CDCl$_3$ solution at 300 MHz). The latter spectrum exhibited absorptions at δ 5.106, 5.949, 6.198, 6.266, 6.341, 6.493, 6.627, and 6.674 (due to the vinyl H's) and broad singlets at δ 1.960, 1.817, 1.686, and 1.615 (ascribed to the vinyl methyl groups in lycopene). The latter data is fully consistent with that reported for lycopene in an article by U. Hengartner, et al., Helv. Chim. Acta, 75, 1848–1865 (1992) [see Column 1 in Table 2 on page 1854 of that article].

NOTE: For a large-scale synthesis of lycopene, use of potassium tert-butoxide as the base is undesirable. More conveniently, one can use sodium methoxide as the base in a solvent mixture of methyl alcohol and dichloromethane—as reported in an alternate route to lycopene. See: European patent application EP 382,067 (Aug. 16, 1990), cited in Chem. Abstracts, 114, 82198e (1991).

What is claimed is:

1. An allenic phosphonate compound of the formula:

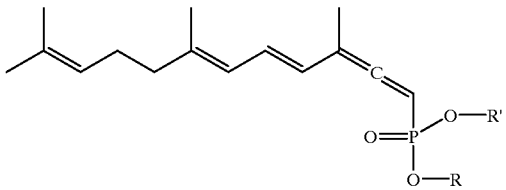

wherein R and R'=C$_1$–C$_4$ alkyl groups; or R, R'=(CH$_2$)$_n$ (n=2 or 3), or [CH$_2$C(CH$_3$)$_2$CH$_2$].

2. The phosphonate of claim 1 which is:
   3,7,11-trimethyl-1,2,4,6,10-dodecapentaenylphosphonic acid, diethyl ester.
3. The phosphonate of claim 1 which is:
   3,7,11-trimethyl-1,2,4,6,10-dodecapentaenylphosphonic acid, dimethyl ester.
4. The phosphonate of claim 1 which is:
   3,7,11-trimethyl-1,2,4,6,10-dodecapentaenylphosphonic acid, diisopropyl ester.
5. The phosphonate of claim 1 which is:
   3,7,11-trimethyl-1,2,4,6,10-dodecapentaenylphosphonic acid, dipropyl ester.
6. The phosphonate of claim 1 which is:
   3,7,11-trimethyl-1,2,4,6,10-dodecapentaenylphosphonic acid, dibutyl ester.
7. The phosphonate of claim 1 wherein R and R' form part of a 5- or 6-membered heterocyclic ring.
8. The phosphonate of claim 7 which is:
   2-(3,7,11-trimethyldodeca-1,2,4,6,10-pentaenyl)-1,3,2-dioxaphospholan-2-one.
9. An allylic phosphonate compound of the formula:

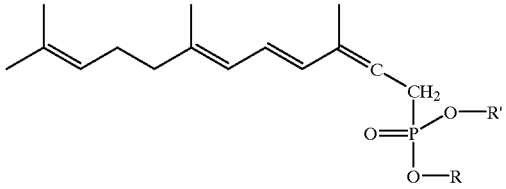

wherein R and R'=C$_1$–C$_4$ alkyl groups.

10. The phosphonate of claim 9 which is:
    3,7,11-trimethyl-2,4,6,10-dodecatetraenylphosphonic acid, diethyl ester.
11. The phosphonate of claim 9 which is:
    3,7,11-trimethyl-2,4,6,10-dodecatetraenylphosphonic acid, dimethyl ester.
12. The phosphonate of claim 9 which is:
    3,7,11-trimethyl-2,4,6,10-dodecatetraenylphosphonic acid, diisopropyl ester.

13. The phosphonate of claim 9 which is:
3,7,11-trimethyl-2,4,6,10-dodecatetraenylphosphonic acid, dipropyl ester.

14. The phosphonate of claim 9 which is:
3,7,11-trimethyl-2,4,6,10-dodecatetraenylphosphonic acid, dibutyl ester.

15. The phosphonate of claim 9 which is:
3,7,11-trimethyl-2,4,6,10-dodecatetraenylphosphonic acid, ethyl beta-hydroxyethyl diester.

16. A method of preparing an allenic phosphonate compound of the formula:

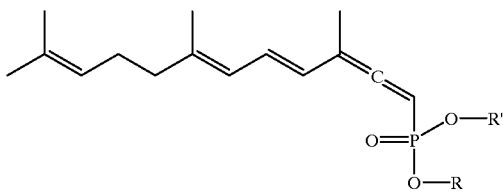

wherein R and R'=$C_1$–$C_4$ alkyl groups; or R, R'=$(CH_2)_n$ (n=2 or 3), or $[CH_2C(CH_3)_2CH_2]$, comprising the steps:
(I) forming a reaction mixture in an aprotic solvent comprising:
(a) ethynyl-pseudoionone;
(b) at least one molar equivalent of a non-nucleophilic base; and
(c) at least one molar equivalent of a dialkyl chlorophosphite reagent; and
(II) maintaining said reaction mixture until said allenic phosphonate is formed.

17. The method of claim 16 wherein said non-nucleophilic base is selected from the group consisting of: tertiary amines, $Na_2CO_3$ and $K_2CO_3$.

18. The method of claim 17 wherein said tertiary amine is pyridine or triethylamine.

19. The method of claim 16 wherein said dialkyl chlorophosphite reagent is selected from the group consisting of: diethyl chlorophosphite and 2-chloro-1,3,2-dioxaphospholane.

20. The method of claim 16 wherein said dialkyl chlorophosphite reagent is added, dropwise, to a solution comprising ethynyl-pseudoionone and at least one molar equivalent of a non-nucleophilic base in an aprotic solvent.

21. The method of claim 16 further including the step of adding water to said reaction mixture after formation of said allenic phosphonate compound to destroy any unreacted dialkyl chlorophosphite reagent.

22. The method of claim 16 wherein said allenic phosphonate compound is selected from the group consisting of:
3,7,11-trimethyl-1,2,4,6,10-dodecapentaenylphosphonic acid, diethyl ester;
3,7,11-trimethyl-1,2,4,6,10-dodecapentaenylphosphonic acid, dimethyl ester;
3,7,11-trimethyl-1,2,4,6,10-dodecapentaenylphosphonic acid, diisopropyl ester;
3,7,11-trimethyl-1,2,4,6,10-dodecapentaenylphosphonic acid, dipropyl ester;
3,7,11-trimethyl-1,2,4,6,10-dodecapentaenylphosphonic acid, dibutyl ester; and
2-(3,7,11-trimethyldodeca-1,2,4,6,10-pentaenyl)-1,3,2-dioxaphospholan-2-one.

23. A method of preparing a C-15 allylic phosphonate compound of the formula:

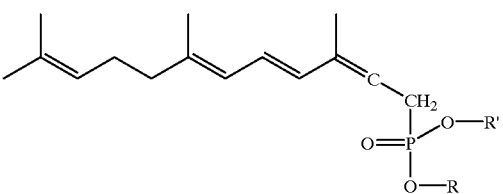

wherein R and R'=$C_1$–$C_4$ alkyl groups, comprising the steps:
(I) forming a first reaction mixture in an aprotic solvent comprising:
(a) ethynyl-pseudoionone;
(b) at least one molar equivalent of a non-nucleophilic base; and
(c) at least one molar equivalent of a dialkyl chlorophosphite reagent;
(II) maintaining said first reaction mixture until said allenic phosphonate is formed; and
(III) partially reducing said allenic phosphonate of step II.

24. The method of step 23 wherein the partial reduction step comprises the steps:
(a) forming a second reaction mixture in an alcohol solvent comprising said allenic phosphonate of step II, ammonium formate, and 10% Pd—C; and
(b) vigorously agitating said second reaction mixture while heating it to a temperature in excess of room temperature.

25. The method of claim 24 wherein said alcohol solvent comprises methyl alcohol.

26. The method of claim 24 wherein said second reaction mixture is heated to a temperature between about 60° C. and about 65° C.

27. The method of claim 23 wherein the partial reduction step comprises forming a second reaction mixture comprising the allenic phosphonate of step II and sodium borohydride.

* * * * *